United States Patent
Omura et al.

(10) Patent No.: US 8,591,571 B2
(45) Date of Patent: Nov. 26, 2013

(54) DRUG-ELUTING STENT

(75) Inventors: Ikuo Omura, Okayama (JP); Zhen Yu Jin, Okayama (JP)

(73) Assignee: Japan Stent Technology Co., Ltd., Okayama (JP)

( * ) Notice: Subject to any disclaimer, the term of this patent is extended or adjusted under 35 U.S.C. 154(b) by 105 days.

(21) Appl. No.: 13/137,560

(22) Filed: Aug. 25, 2011

(65) Prior Publication Data

US 2011/0313514 A1    Dec. 22, 2011

Related U.S. Application Data

(63) Continuation of application No. PCT/JP2010/052975, filed on Feb. 25, 2010.

(30) Foreign Application Priority Data

Mar. 2, 2009  (JP) ................................. 2009-048577

(51) Int. Cl.
A61F 2/06   (2013.01)
A61F 13/00  (2006.01)
A61F 2/00   (2006.01)

(52) U.S. Cl.
USPC .......... 623/1.42; 424/422; 424/423; 424/424; 424/425

(58) Field of Classification Search
USPC .................. 623/1.42; 424/422, 423, 424, 425
See application file for complete search history.

(56) References Cited

U.S. PATENT DOCUMENTS

| | | | |
|---|---|---|---|
| 7,033,602 B1 | 4/2006 | Pacetti et al. | |
| 7,179,285 B2 | 2/2007 | Ikeuchi et al. | |
| 7,229,471 B2 | 6/2007 | Gale et al. | |
| 7,357,942 B2 | 4/2008 | Burke et al. | |
| 7,378,105 B2 | 5/2008 | Burke et al. | |
| 7,625,399 B2 | 12/2009 | Case et al. | |
| 7,691,401 B2 | 4/2010 | Castro et al. | |
| 7,985,251 B2 | 7/2011 | Ikeuchi et al. | |
| 8,157,857 B2 | 4/2012 | Case et al. | |
| 8,221,495 B2 | 7/2012 | Shrivastava et al. | |
| 2003/0158596 A1 | 8/2003 | Ikeuchi et al. | |
| 2004/0034409 A1 | 2/2004 | Heublein et al. | |
| 2004/0117007 A1* | 6/2004 | Whitbourne et al. | 623/1.42 |
| 2005/0015136 A1 | 1/2005 | Ikeuchi et al. | |
| 2005/0060028 A1 | 3/2005 | Horres et al. | |
| 2005/0176678 A1 | 8/2005 | Horres et al. | |
| 2006/0036311 A1 | 2/2006 | Nakayama et al. | |
| 2006/0093771 A1* | 5/2006 | Rypacek et al. | 428/36.91 |
| 2007/0141112 A1 | 6/2007 | Falotico et al. | |
| 2008/0038307 A1 | 2/2008 | Hoffmann | |
| 2009/0005861 A1 | 1/2009 | Hossainy et al. | |
| 2009/0005862 A1 | 1/2009 | Nakatani et al. | |
| 2009/0048667 A1 | 2/2009 | Mochizuki et al. | |
| 2010/0198344 A1 | 8/2010 | Omura et al. | |
| 2010/0249914 A1 | 9/2010 | Omura et al. | |
| 2011/0060403 A9 | 3/2011 | Nakatani et al. | |
| 2012/0310329 A1* | 12/2012 | Omura et al. | 623/1.42 |
| 2013/0018455 A1* | 1/2013 | Omura et al. | 623/1.43 |

FOREIGN PATENT DOCUMENTS

| | | |
|---|---|---|
| CN | 1568166 A | 1/2005 |
| CN | 1925881 A | 3/2007 |
| JP | 7-196650 | 8/1995 |
| JP | 2001-190687 | 7/2001 |
| JP | 2002-000739 | 1/2002 |
| JP | 2003-24452 | 1/2003 |
| JP | 2003-33439 | 2/2003 |
| JP | 2003-190294 | 7/2003 |
| JP | 2004-267368 | 9/2004 |
| JP | 2005/170801 | 6/2005 |
| JP | 2005-530551 | 10/2005 |
| JP | 2005-534724 | 11/2005 |
| JP | 2007-190369 | 8/2007 |
| JP | 2007-195883 | 8/2007 |
| JP | 2007-229123 | 9/2007 |
| JP | 2008-523901 | 7/2008 |
| JP | 2008-179788 | 8/2008 |
| WO | 00/15271 | 3/2000 |
| WO | 02/080996 A1 | 10/2002 |
| WO | 2004/000379 A1 | 12/2003 |
| WO | 2004/022150 A1 | 3/2004 |
| WO | 2005/097224 A1 | 10/2005 |
| WO | 2006/065685 A2 | 6/2006 |
| WO | 2007/058190 A1 | 5/2007 |
| WO | WO 2007/086269 A1 | 8/2007 |
| WO | 2007/148714 A1 | 12/2007 |
| WO | 2009/031295 A1 | 3/2009 |

OTHER PUBLICATIONS

Mureebe et al., Ann Vasc. Surg., 2004, 8, 147-150.*
International Search Report for PCT/JP2010/052975, Mailed Apr. 20, 2010.
Chinese Office Action mailed Mar. 22, 2013 for corresponding Chinese Application No. 200880105243.4.

(Continued)

*Primary Examiner* — Abigail Fisher

(57) ABSTRACT

A drug-eluting stent comprises a coated layer prepared of a composition comprising a polymer and a drug, the coated layer being a single coated layer with the composition, or comprises a first coated layer prepared of the above composition and a second coated layer with a polymer alone, the first coated layer being coated by the second coated layer. The drug is a vascular intimal hyperplasia inhibitor which does not inhibit proliferation of endothelial cells, and the composition substantially excludes a lipid-soluble low-molecular compound. The polymer in the first layer is a copolymer of lactic acid (monomer A) and a terminal hydroxy straight alkyl carboxylic acid having 3 to 8 carbon atoms, and, if the second coated layer is formed, the polymer in the second coated layer is a poly(lactic acid), a poly(glycolic acid), or a poly(lactic acid-co-glycolic acid).

8 Claims, 1 Drawing Sheet

(56) References Cited

OTHER PUBLICATIONS

U.S. Office Action mailed May 17, 2013 for possibly related U.S. Appl. No. 13/492,290.
U.S. Appl. No. 12/733,460, filed Mar. 3, 2010, Ikuo Omura, Japan Stent Technology Co., Ltd., Tokai University Educational System, Toyo Advanved Technologies Co., Ltd., Hiroo Iwata.
U.S. Appl. No. 13/492,290, filed Jun. 8, 2012, Ikuo Omura, Japan Stent Technology Co., Ltd., Tokai University Educational System, Toyo Advanced Technologies Co., Ltd., Hiroo Iwata.
U.S. Appl. No. 13/561,828, filed Jul. 30, 2012, Ikuo Omura, Japan Stent Technology Co., Ltd., Tokai University Educational System, Toyo Advanced Technologies Co., Ltd., Hiroo Iwata.
Japanese Office Action issued May 21, 2013 in related Japanese Application No. 2009-531112.
Extended European Search Report issued May 24, 2013 in related European Application No. 08829751.0.
Notice of Allowance mailed from the United States Patent and Trademark Office on Sep. 30, 2013 in U.S. Appl. No. 13/492,290.

* cited by examiner

Stent1

2.0 mm

PATHOLOGICAL SPECIMEN OF DES 2

DRUG-ELUTING STENT

CROSS REFERENCE TO THE RELATED APPLICATION

This application is a continuation application, under 35 U.S.C. §111(a), of International Application No. PCT/JP2010/052975, filed Feb. 25, 2010, which claims priority to Japanese Patent Application No. 2009-048577, filed Mar. 2, 2009, the disclosures of which is herein incorporated by reference in their entirety into this application.

FIELD OF THE INVENTION

The present invention relates to a drug-eluting stent useful for treatment of constricted blood vessels, to a method of making the same, and to a method of controlling the elution rate of the drug from the stent. More specifically, the present invention relates to a stent carrying a vascular intimal hyperplasia inhibitor, which does not inhibit proliferation of endothelial cells and showing a sustained release over a long period of time, to a method of making such stent, and to a method of controlling the elution rate of the inhibitor from the stent.

BACKGROUND ART

In recent years, the stent treatment has become popular in the field of medical treatment, in which an affected area of the coronary artery having been constricted as a result of progress of arteriosclerosis is mechanically expanded with the aid of a balloon catheter, followed by placement of a metallic stent within the vascular lumen to restore the flow of blood. Development of the stent treatment is indeed a good news to patients suffering from arterial stenosis. However, placement of such a stent in the coronary artery, of which constriction or occlusion is highly fatal, has been found that involving the probability of postoperative treatment required reaches 20 to 30% because even though the stent has been placed, vascular intimal hyperplasia occurs with the vascular lumen narrowed consequently. In view of the above, in order to decrease the in-stent restenosis, attempts have been made to design a stent of a type having a surface carrying a drug effectively to exhibit restenosis prevention effects so that the drug, when the stent is placed in an artery, can be eluted in a controlled manner within the vascular lumen to thereby suppress the restenosis. Those attempts have led to commercialization of drug-eluting stents (hereinafter referred to as DES) utilizing sirolimus (immunosuppressor) and paclitaxel (anticancer drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation of endothelial cells once denuded during placement of the stent is also suppressed, resulting in adverse effect that the repair or treatment of the intima of a blood vessel becomes retarded. In view of the fact that thrombosis tends to occur easily at the site being not covered with endothelial cells in the intima of a blood vessel, an antithrombotic drug must be administrated for a prolonged time, say, half a year or so and, even though the antithrombotic drug is administrated, there is a risk that the late thrombosis may lead to sudden death.

The first event occurring in the causal sequence from the intravascular stent placement to the in-stent restenosis is said to be an "injury to the blood vessel at the time of placement of the stent, particularly an injury to the endothelial cells", which leads to a causal consequence of "formation of blood clots", "adhesion or infiltration of leukocytes into the blood vessel wall", "inflammation", "proliferation of smooth muscle cells" and "stenosis" in this order. Accordingly, it is expected that suppression of the formation of blood clots is effective to inhibit the stenosis and, based on this view, application of an antithrombotic drug such as, for example, heparin or hirudin to form a drug-eluting stent has been strenuously tried at the initial stage of development thereof, but the clinical effectiveness thereof has not been ascertained. Now that the drug-eluting stent utilizing sirolimus or paclitaxel has been widespread in these days, the drug-eluting stent coated with the antithrombotic drug has been a minor candidate in the development of drug-eluting stents. At present, however, the practicality of the drug-eluting stent carrying a vascular intimal hyperplasia inhibitor, which does not inhibit proliferation of endothelial cells, has not yet been proved.

On the other hand, the Patent Document 1 listed below discloses in an embodiment of the invention thereof, a stent capable of eluting both of argatroban (anticoagulant agent) and cilostazol (antiplatelet agent). The Patent Document 2 also listed below discloses the elution rate of the drug from a polymer film containing argatroban, immersed in a solution of phosphate buffer (pH 7.4) for three weeks. In any event, however, surprising effect of inhibiting the vascular intimal hyperplasia while the drug is carried by the stent has not yet been observed.

PATENT DOCUMENT

[Patent Document 1] JP Laid-open Patent Publication No. 2001-190687
[Patent Document 2] WO2007/058190

DISCLOSURE OF THE INVENTION

Problems to be Solved by the Invention

An object of the present invention is to provide a stent carrying a vascular intimal hyperplasia inhibitor of a kind, which does not inhibit proliferation of endothelial cells, in which stent is capable of releasing the drug in a controlled manner over a long period, and a method of making such a stent.

Another object of the present invention is to provide a method of controlling the elution rate of the drug from the stent carrying the drug.

Means of Solving the Object

According to a first aspect of the present invention, there is provided a drug-eluting stent comprising a stent body of a cylindrical configuration having outer and inner surfaces, and a coated layer coating at least the outer surface of the stent body, the coated layer being a single coated layer and prepared of a composition comprising a polymer and a drug, the composition substantially excluding a lipid-soluble (or lipophilic) low-molecular compound, the drug is a vascular intimal hyperplasia inhibitor which does not inhibit proliferation of endothelial cells, the weight compositional ratio (Y/X) of the vascular intimal hyperplasia inhibitor (Y) based on the polymer (X) being within the range of 1/9 to 6/4, the polymer being a copolymer of lactic acid (monomer A) and a terminal hydroxy straight alkyl carboxylic acid having 3 to 8 carbon atoms (monomer B), and the copolymerization mole ratio (A/B) of the monomer A and the monomer B being within the range of 8/2 to 2/8.

In the practice of the present invention, the term "stent" referred to hereinabove and hereinafter is intended to mean a tubular medical instrument, which is, when a blood vessel or any other lumen within a living body is constricted or occluded, placed at the affected area of the blood vessel or lumen to expand the constricted or occluded site to secure a required lumen region. The stent of the kind referred to above has a diameter small enough for it to be inserted into the living body and is used to expand the constricted area to thereby increase the lumen diameter and then to maintain the affected area in an expanded state.

Also, in the practice of the present invention, the term "polymer" referred to hereinabove and hereinafter is used as a term intended to encompass a homopolymer, a copolymer and a mixture of polymers.

The term "composition" referred to hereinabove and hereinafter as employed in the practice of the present invention is intended to mean a composition comprising a polymer and a drug, with the drug being dispersed in a polymer matrix (including either a dense structure or a porous structure) in the form of molecules or microdispersed solids.

The vascular intimal hyperplasia inhibitor of a kind which does not inhibit proliferation of endothelial cells, employed in the practice of the present invention includes, for example, argatroban, ximelagatran, melagatran, dabigatran and dabigatoran etexilate, but of them argatroban is preferably employed for the inhibitor. Accordingly, in the description of the present invention that follows, reference will be made to the use of argatroban as an example of the vascular intimal hyperplasia inhibitor of the specific kind.

The argatroban employed in the practice of the present invention has a general term of (2R,4R)-4-methyl-1-[N2-((RS)-3-methyl-1,2,3,4-tetrahydro-8-quinoline sulfonyl)-L-arginyl]-2-piperidine carboxylic acid hydrate that is expressed by the following chemical structural formula. It is to be noted that argatroban is well known in the art as a compound having an antithrombin effect. (See the Patent Documents 1 and 2 referred to hereinbefore.) However, it had not been known that the argatroban had an effect of inhibiting the vascular intimal thickening, without inhibiting proliferation of endothelial cells. The inventors of the present invention found that the argatroban eluted from a stent by the moderate elution rate had an effect of inhibiting the vascular intimal hyperplasia, without inhibiting proliferation of endothelial cells, and disclosed the above findings in the specification of the international patent application of PCT/JP 2008/002410. The present specification describes hereinafter the examples described in the above specification as Reference Example. The present invention has been completed based on the above findings.

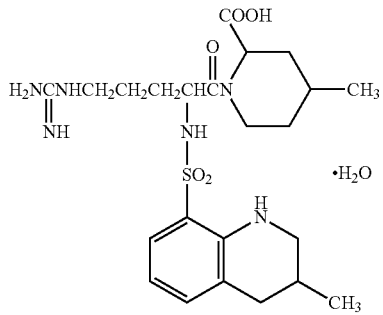

In a preferred embodiment of the first aspect of the present invention, the single coated layer preferably has a thickness within the range of 1 to 20 μm.

In a preferred embodiment of the first aspect of the present invention, the monomer B is preferably 6-hydroxy hexanoic acid.

In a preferred embodiment of the first aspect of the present invention, the low-molecular compound preferably has a molecular weight of 400 or less.

According to a second aspect of the present invention, there is also provided a drug-eluting stent comprising a stent body of a cylindrical configuration having outer and inner surfaces, and a first coated layer coating at least the outer surface of the stent body. The first coated layer is prepared of a composition comprising a polymer (a first polymer) and a drug, and coated by a second coated layer being prepared of a polymer (a second polymer) alone. The composition substantially excludes a lipid-soluble low-molecular compound. The drug is a vascular intimal hyperplasia inhibitor of a kind, which does not inhibit proliferation of endothelial cells, the weight compositional ratio (Y/X) of the vascular intimal hyperplasia inhibitor (Y) based on the first polymer (X) being within the range of 1/9 to 6/4. The polymer of the first coated layer is a copolymer of lactic acid (monomer A) and a terminal hydroxy straight alkyl carboxylic acid having 3 to 8 carbon atoms (monomer B), and the copolymerization mole ratio (A/B) of the monomer A and the monomer B is within the range of 8/2 to 2/8. The polymer of the second coated layer is a poly(lactic acid), a poly(glycolic acid), or a poly(lactic acid-co-glycolic acid), and substantially excludes a lipid-soluble low-molecular compound.

In a preferred embodiment of the second aspect of the present invention, the vascular intimal hyperplasia inhibitor preferably comprises argatroban as an essential component.

In a preferred embodiment of the second aspect of the present invention, the first coated layer preferably has a thickness within the range of 1 to 20 μm and the second coated layer preferably has a thickness of not thinner than 0.1 μm and thinner than 0.5 μm.

In a preferred embodiment of the second aspect of the present invention, the monomer B is preferably 6-hydroxy hexanoic acid; and the low-molecular compound preferably has a molecular weight of 400 or less.

Furthermore according to a third aspect of the present invention, there is provided a method of making a stent comprising a stent body and a coated layer, which comprises: applying the composition including the polymer and the drug as mentioned in embodiments of the first and second aspects to at least an outer surface of the stent body with the use of a solution containing a fluorinated alcohol solvent or a mixed solvent comprising a fluorinated alcohol as a major component, removing the solvent to thereby form the coated layer.

Furthermore according to a fourth aspect of the present invention, there is provided a method of controlling the elution rate of argatroban from a stent in which the composition referred to above is applied to a surface of the stent body with the use of the solution comprising the composition dissolved with the solvent, followed by removal of the solvent to thereby form a coated layer (for example, the single coated layer in the first aspect of the present invention or the first coated layer in the second aspect of the present invention), the solvent dissolving the composition containing a fluorinated alcohol as a major component, and optionally containing a non-fluorinated alcohol, a ketone, an ester, or a halogenated hydrocarbon, and in which the elution rate is controlled by changing the copolymerization ratio of the monomer A and the monomer B in the copolymer of lactic acid (monomer A)

and a terminal hydroxy straight alkyl carboxylic acid having 3 to 8 carbon atoms (monomer B), and/or by changing the concentration of the fluorinated alcohol in the solvent by adding a non-fluorinated alcohol, a ketone, an ester, or a halogenated hydrocarbon to the solvent.

Effect of the Invention

According to the first aspect of the present invention discussed hereinabove, since (i) the single coated layer comprises a polymer (X) and a vascular intimal hyperplasia inhibitor (Y) which does not inhibit proliferation of endothelial cells, (ii) the weight compositional ratio (Y/X) of the vascular intimal hyperplasia inhibitor (Y) based on the polymer (X) is within the range of 1/9 to 6/4, (iii) the coated layer contains a vascular intimal hyperplasia inhibitor in a larger quantities, and (iv) the polymer forming the coated layer is a copolymer of lactic acid (monomer A) and a hydroxy alkyl carboxylic acid (monomer B) in which the copolymerization mole ratio (A/B) of the monomer A and the monomer B is within the range of 8/2 to 2/8, the vascular intimal hyperplasia inhibitor can be released persistently at a proper elution rate. As a result, the stent capable of exhibiting the effect of inhibiting the vascular intimal hyperplasia without inhibiting proliferation of endothelial cells can be obtained.

Further, according to the first aspect of the present invention, since the single coated layer is formed from the composition which does not contain a lipid-soluble low-molecular compound capable of eluting into the blood, the stent has not only a high pharmacological effect as mentioned above but also high safety, and does not show injurious effects on a human body.

Also, since the stent of the structure according to the first aspect of the present invention described hereinabove comprises a coated layer prepared of a polymer, i.e., a copolymer of lactic acid and a terminal hydroxy straight alkyl carboxylic acid having 3 to 8 carbon atoms, even with the single layer, the stent attains a sustained release of drugs such that the drug release is observed over 48 hours after immersion of the stent in the phosphate buffered saline at 37° C.

In the second aspect of the present invention, since the coated layer of the first aspect (i.e., a first coated layer) is coated with a second coated layer comprising a poly(lactic acid), a poly(glycolic acid), or a poly(lactic acid-co-glycolic acid), and substantially excluding a lipid-soluble low-molecular compound, even when the polymer of the first coated layer has a tacky property, direct contact between the tacky polymer and blood can be prevented without inhibiting the drug elution from the first coated layer.

In the practice of the third aspect of the present invention described hereinabove, a fluorinated alcohol solvent or a mixed solvent containing a fluorinated alcohol as a major component is used as a solvent for dissolving the composition. Since the use of this kind of solvents is effective to dissolve both the polymer and the drug (argatroban), the coated layer prepared of the composition comprising the polymer and the drug (argatroban) with the use of this solvent contributes to sustained release of the drug, and further, the control of the drug elution rate can be characteristically easily accomplished by using a mixed solvent comprising a fluorinated alcohol solvent in combination with a solvent of a non-fluorinated alcohol, a ketone, or an ester type.

According to the forth aspect of the present invention described hereinabove, the elution rate of argatroban can be controlled within a desired range (i) by changing the copolymerization ratio of the lactic acid and the hydroxy alkyl carboxylic acid constituting the polymer of the single coated layer in the first aspect of the present invention or the first coated layer in the second aspect of the present invention, and/or (ii) by using only a fluorinated alcohol as a solvent for dissolving the composition or by changing a concentration of the fluorinated alcohol in the solvent by adding a non-fluorinated alcohol, a ketone, an ester, or a halogenated hydrocarbon to the solvent.

According to the present invention, argatroban contained in the coated layer formed on the stent body can be eluted from the stent body at a rate of 3 $\mu g/cm^2$ per day or higher for at least two days subsequent to placement of the stent within the blood vessel, particularly the artery. In view of this, the argatroban so eluted can exhibit its inherent pharmacologic effect (suppression of vascular intimal hyperplasia) to thereby inhibit the occurrence of an in-stent restenosis. Also, in view of the fact that the whole intimal surfaces are covered by the endothelial cells one month after the stent has been placed, such a significant effect can be achieved that the incidence of thrombosis, particularly late thrombosis is minimized as compared with the existing drug-eluting stent.

The drug-eluting stent according to the present invention can be effectively utilized in the practice of a stent treatment of the coronary artery, but can also be equally effectively utilized in the practice of a stent treatment of any other artery such as, for example, brain artery, renal artery and peripheral arteries.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims.

DETAILED DESCRIPTION OF EMBODIMENTS (Stent Structure)

Figure 1:
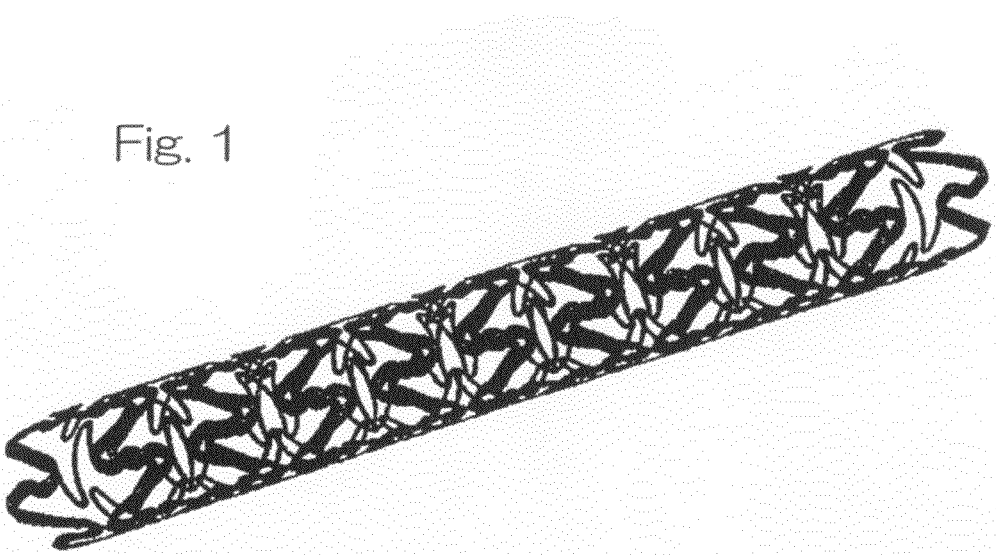
FIG. 1 is a perspective view showing one example of the shape of a stent body employed in the practice of the present invention.

Material that can be used to form a stent body is not specifically limited to a particular material, and any of those metallic, ceramic and polymer materials hitherto known in the pertinent art can be employed. However, of them, the metallic material having a high rigidity and a high corrosion resistance is preferred as a material for the stent body. Examples of such metallic material include stainless steel, tantalum, a nickel-titanium alloy (including nitinol), a magnesium alloy and a cobalt alloy (including an alloy containing cobalt, chromium and nickel). The stent body is of a structure having a cylindrical configuration and also having an outer surface and an inner surface opposite to the outer surface and may be a balloon expandable type, a self-expandable type or a combination thereof. FIG. 1 is a perspective view showing an example illustrating the shape of the stent body that is used in the practice of the present invention, particularly as a drug-eluting stent. The mesh design of the stent body and the shape of struts are not specifically limited to particular ones, provided that a factor contributing to the in-stent restenosis, for example, a turbulent flow of blood in the vicinity of the inner wall of vessels and/or the mechanical stimulus brought by the projection of a bent portion of the struts to the blood vessel, so called a fish scale phenomenon, is below average. In any event, for the stent body utilized in the practice of the present invention, a stent body made of a cobalt alloy such as disclosed in the Japanese patents No. 3654627 and No. 3605388 may be employed, the disclosure of each of which is herein incorporated by reference as a part of this specification. The stent body having a predetermined shape can be formed by means of a processing with the use of a laser processing machine or the like and subsequent surface finishing such as, for example, surface grinding or polishing.

(Surface Treatment of Stent Body)

When the coating solution so prepared in the manner described above is applied to the stent body surface, it is necessary for the coated layer, left after volatilization of the solvent, to adhere to the stent body surface, and, therefore, prior to the coating, if necessary, the stent body surface is preferably cleansed or activated. The surface treatment for this purpose may be performed by either singly or a combination of chemical treatment utilizing an oxidizing reagent or fluorine gas, surface graft polymerization, plasma discharge treatment, corona discharge treatment, UV/ozone treatment and electron irradiation.

(Compositional Ratio of Polymer to Drug in the Principal Coated Layer)

The principal coated layer (hereinafter both the single coated layer in the first aspect of the present invention and the first coated layer in the second aspect of the present invention are sometimes referred to as a principal coated layer) is prepared of a composition containing a polymer and a drug (argatroban). The weight compositional ratio of the polymer to the drug (argatroban) in the composition is within the range of 4:6 to 9:1 (the sum of the both being 10). If the proportion of the drug (argatroban) is less than 1, the elution rate of the drug (argatroban) from the coated layer is too low, but if it exceeds 6, the coated layer will become fragile, making it difficult to adhere to the stent base material. In addition, the higher the ratio of the drug to the polymer is, the larger the elution amount in the early stage of usage is.

(First Polymer Comprising the Composition)

In the practice of the present invention, the focus is placed on the capability of eluting the drug (argatroban) in a quantity effective to suppress stenosis persistently for a predetermined period of time. For this purpose, in the composition, a copolymer of lactic acid (monomer A) and a terminal hydroxy straight alkyl carboxylic acid having 3 to 8 carbon atoms (monomer B) is used as a matrix polymer necessary for the drug (argatroban) to be carried. With the use of this polymer, the stent attains a sustained release of the drug (argatroban) over a long period of time, preferably over 48 hours, still preferably over 72 hours, after immersion of the stent in the phosphate buffered saline at 37° C. It should be noted that a terminal hydroxy straight alkyl carboxylic acid having 3 to 8 carbon atoms is used as the monomer B as mentioned above. With the carboxylic acids outside the above range, for example, hydroxy ethanoic acid having 2 carbon atoms causes too strong elution whereas hydroxy nonoic acid having 9 carbon atoms causes lower elution than desired.

The monomer A may be L-lactic acid or D-lactic acid. Specific examples of monomer B may include 3-hydroxy propanoic acid (C3), 4-hydroxy butanoic acid (C4), 5-hydroxy pentanoic acid (C5), 6-hydroxy hexanoic acid (C6), 7-hydroxy heptanoic acid (C7), 8-hydroxy octanoic acid (C8), and 3-(2-hydroxyethoxy) propanoic acid (C5). Of these, a copolymer of 6-hydroxy hexanoic acid (C6) (or ε-hydroxy caproic acid) and lactic acid can be preferably used in the present invention.

The elution property of the drug is dependent on the copolymerization ratio of the monomer A and the monomer B, and when the ratio A/B is within the range of 8/2 to 2/8, the stent can elute an effective quantity of the drug continuously. The elution rate from the principal coated layer is dependent on the rate of diffusion of the drug in the polymer, and the rate of degradation of the polymer. Accordingly, by adjusting two parameters, that is, the rate of diffusion of the drug in the polymer and the rate of degradation of the polymer, the drug elution rate can be controlled. In order to increase the rate of diffusion of the drug in the polymer, selection of higher ratio of the monomer B contributes to form a polymer having a low glass transition temperature by itself, whereas in order to increase the biodegrading rate, selection of a copolymer having a copolymerization ratio of 1:1 is appropriate. Further, since the polymer having the copolymerization ratio of the above range shows biodegradability, the polymer tends to vanish in the living body within 1 year after implanted, and is therefore advantageously used. From the viewpoint of securing the strength of the coated layer as well as working efficiency of coating, it is appropriate for the polymer to have a molecular weight of 20,000 to 500,000.

(Low-Molecular Compound)

In the present invention, since the copolymer of lactic acid and a hydroxy alkyl carboxylic acid is used as a polymer to form a principal coated layer, the drug (argatroban) contained in this polymer can be released at a moderate elution rate. For this reason, the composition which constitutes the principal coated layer does not necessary include a release auxiliary agent (a carboxylic acid ester, a monoester or diester of glycerol, preferably dimethyl tartrate, diethyl tartrate, etc.) which is a type of lipid-soluble low-molecular compounds disclosed in the Patent Document 2. Where a low-molecular compound (usually having a molecular weight of 400 or less), such as the above release auxiliary agent, a plasticizer, and an emulsifier, is included in a coating material for the stent, the low-molecular compound may be easy to elute into blood when a stent is applied to the inside of the body. Accordingly, it is not desirable to use a low-molecular compound in respect of the safety to human body. Therefore, in the present invention, the above-mentioned principal coated layer substantially excludes a kind of the above-mentioned low-molecular compounds. It should be noted that the term "substantially exclude" referred to hereinabove and hereinafter is intended to mean that the polymer does not contain the low-molecular compound at a ratio of 5 parts by weight or more, preferably 1 part by weight or more relative to 100 parts by weight of the polymer.

(Thickness of Principal Coated Layer)

The thickness of the principal coated layer of the stent is preferably within the range of 1 to 20 μm, more preferably within the range of 2 to 15 μm, in order for the drug (argatroban) to be eluted in proper quantity. If the thickness of the principal coated layer exceeds 20 μm, there is a risk that the intra-stent constriction will become large and, therefore, the thickness of the principal coated layer is preferred not to exceed 20 μm. Accordingly, in order that the thickness of the principal coated layer does not exceed 20 μm, it is necessary to control the formulation of the coating solution and the coating condition, such as duration or the number of times the coating liquid is in contact with the stent.

(Formation of Principal Coated Layer)

In the practice of the present invention, at least an outer surface of a cylindrical surface of the stent body of the structure described above, preferably outer and inner surfaces thereof is/are formed from a principal polymer coated layer, in which the drug is carried in the principal coated layer. As a method of making the drug carried by the stent body surface, there may be mentioned a dipping method in which the stent is immersed in a coating solution prepared by dissolving a drug and a polymer with the use of a suitable solvent, followed by removal from the coating solution to dry; a spray method in which a solution comprising a drug and a polymer dissolved therein with the use of a solvent is sprayed onto the stent; and a simultaneous spray method using two nozzles in which a drug and a polymer, which have been separately dissolved in respective solvents, are sprayed simultaneously onto the stent, and any of those methods can be employed in the practice of the present invention.

In the practice of the present invention, the composition containing the drug (argatroban) is coated on at least the outer surface of the stent body (the surface of the stent body which is in contact with the wall of the blood vessel) of the cylindrical configuration. In such case, the coating solution containing the composition dissolved in the solvent is preferably applied to the outer surface of the stent body by means of a spraying technique. Also, where not only the outer surface of the stent body, but also the inner surface thereof are desired to be coated, the solution so prepared may be sprayed onto both of those stent body surfaces. Alternatively, application of such coating solution to the stent body surfaces may be accomplished by dipping the stent body into the solution. Removal of the solvent after the coating may be suitably accomplished by means of depressurization, air blasting or heating.

(Selection of Solvent for Preparation of Composition)

As a volatile solvent having a boiling point of lower than 100° C. and capable of dissolving the drug (argatroban) and readily removable from the stent body after coating, there may be mentioned methanol, ethanol, trifluoroethanol, hexafluoroisopropanol and a mixed solvent comprising the above mentioned alcohol(s). Moreover, as a solvent dissolving the polymer illustrated above, there may be mentioned trifluoroethanol, hexafluoroisopropanol, ketones such as acetone, esters such as ethyl acetate, and halogenated hydrocarbons such as dichloromethylene. As an appropriate solvent which dissolves both the drug (argatroban) and the above-mentioned polymer and imparts a sustained release of the drug, there may be mentioned fluorinated alcohols with 2 to 4 carbon atoms (trifluoroethanol, hexafluoroisopropanol, pentafluoropropanol, octafluorobutanol, etc.) and a mixed solvent comprising the above fluorinated alcohol as a major component. The mixed solvent comprising a fluorinated alcohol as a major component comprises the fluorinated alcohol at the proportion of 50% or higher, in combination with other solvent(s) such as non-fluorinated alcohols (methanol, ethanol, propanol, butanol, etc.), esters (methyl acetate, ethyl acetate, amyl acetate, methoxybutyl acetate, etc.), ketones (acetone, methyl ethyl ketone, methyl isobutyl ketone, etc.), or halogenated hydrocarbons (dichloromethylene, trichloroethylene, tetrachloroethylene, etc.). The lower proportion of the fluorinated alcohol attained by mixing the fluorinated alcohol with other above-mentioned solvents, results in higher elution rate of the drug. Thereby, the elution rate can be controlled to a desired rate.

(Formation of Second Coated Layer)

In the practice of the present invention, the principal coated layer comprising a drug-containing polymer has a one-layered coated structure (single coated layer) having a thickness of within the range of 1 to 20 μm, and the desired elution rate can be achieved by this single coated layer. Accordingly, it is not necessary to control the elution rate of the drug by changing the coated layer into a bi-layer structure, i.e., a structure further comprising a coated layer (B) on the drug-containing coated layer (A), and changing polymer materials contained in the coated layer (B) or thickness thereof. In addition, when the stent of the present invention is used under body temperature, in the case where the polymer of the above-mentioned principal coated layer has an tacky feature, it is desirable to form the second coated layer consisting essentially of a polymer on the above-mentioned principal coated layer (that is the first coated layer) in order to prevent direct contact of the drug-containing polymer with blood. The phrase "the layer consisting essentially of a polymer" referred to hereinabove and hereinafter is intended to mean that the layer does not contain substantially any components other than a polymer (the layer does not contain a drug, such as antithrombin agents, immunosuppressants, and anticancer agents, lipid-soluble low-molecular compounds, saccharides, amino acids, inorganic and organic salts).

As a polymer used for forming the second coated layer, a biodegradable polymer having a glass transition temperature of 0° C. or higher, such as a poly(lactic acid), a poly(glycolic acid), and a poly(lactic acid-co-glycolic acid), is preferably used. Although the copolymerization ratio (lactic acid:glycolic acid) of the poly(lactic acid-co-glycolic acid) may be arbitrarily selected from the range of 100:0 to 0:100, the preferable copolymerization ratio may be 50:50, 65:35, or 75:25.

The coating method includes dissolving the above-mentioned polymer in a solvent (a fluorinated alcohol, a non-fluorinated alcohol, a ketone, an ester, etc.), and forming a second coated layer on the above-mentioned principal coated layer in the same way as described in the formation of the principal coated layer. The thickness of the second coated layer may be a thickness such that direct contact between the principal coated layer and blood can be prevented, and can be chosen within the range of 0.1 μm or more and less than 0.5 μm. If thickness is too large, the elution of the drug from the principal coated layer may be affected. The second coated layer as well as the principal coated layer does not contain a lipid-soluble low-molecular compound, such as a release auxiliary agent disclosed in the Patent Document 2.

(Control of Drug Elution Rate)

In order for the drug-eluting stent according to the present invention to markedly suppress the in-stent restenosis, it is of therapeutic benefit to release argatroban at a rate of 3 μg/cm$^2$ per day or higher for at least first two days subsequent to the intravascular placement of the stent. According to the present invention, as described above, since the composition comprising 10 to 60 wt % of the drug (argatroban) and 90 to 40 wt % of the polymer is uniformly coated on at least the outer surface of the cylindrical stent body to provide the coated layer having a thickness within the range of 1 to 20 μm, the elution rate of the argatroban can be controlled at a rate of 3 μg/cm$^2$ per day or higher, preferably 4 μg/cm$^2$ per day or higher, and more preferably 6 μg/cm$^2$ per day or higher for at least two days subsequent to the immersion of the stent in the phosphate buffered saline of 7.4 in pH value at 37° C., thereby, when inserted into an artery, thus obtained stent can maintain the elution of the argatroban even after a predetermined period.

EXAMPLES

Hereinafter, the present invention will be specifically demonstrated by way of examples, which are described only for the purpose of illustration and are not intended to limit the scope of the present invention. Materials, numerical values of, for example, the amounts of use, the concentrations and processing temperatures, and processing methods, which are employed and set forth in the following examples are of course only for the purpose of illustration and should not be construed as limiting the scope of the present invention.

Reference Example

It has been confirmed in the following example that the argatroban has an effect of inhibiting the vascular intimal hyperplasia, without inhibiting proliferation of endothelial cells. The coated layer in the Preparing Reference Example as described below relates to the invention disclosed in the specification of International Patent Application PCT/JP2008/002410 conducted by inventors including the inventors of the present invention. Although it differs from the coated layer of the present invention, the results obtained in Reference Example had revealed that the argatroban had an effect of suppressing the vascular intimal thickening, without inhibiting proliferation of endothelial cells.

(1) Preparing Reference Example 1

(1-1) A mixed solution (coating solution) was prepared by dissolving 140 mg of argatroban and 160 mg of poly(D, L-lactic acid-co-glycolic acid) (mole ratio: 50/50) uniformly with the use of 20 mL of 2,2,2-trifluoroethanol. A stent body (hereinafter referred to as Stent 1) of such a design as shown in FIG. 1 and having the total surface of 0.70 cm$^2$, a length of 17 mm, an inner diameter of 3 mmφ when dilated, and an outer diameter of 1.55 mmφ when processed, was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 30 stent bodies were coated in the manner described above. When those stent bodies were measured to the unit of μg by means of a microbalance, it has been found that an average quantity of 619 μg of the mixture containing argatroban and the copolymer referred to above was coated on those stent bodies (Average thickness of the coated layer: 7.4 μm). Those stent bodies are hereinafter referred to as DES 1.

(1-2) A mixed solution (coating solution) was prepared by dissolving 300 mg of poly(D, L-lactic acid-co-glycolic acid) (mole ratio: 50/50) uniformly in 20 mL of chloroform. The DES 1 prepared in (1-1) described above was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 100 seconds to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions, 15 stent bodies were coated in the manner described above. When those stent bodies were measured by means of a microbalance, it has been found that the copolymer referred to above was coated in a quantity of 103 μg on average. (Average thickness of the second coated layer: 1.2 μm) Hereinafter, the stent bodies formed with those two layers (Coating Total Amount: 722 μg, and Average Coated Layer Thickness: 8.6 μg) are hereinafter referred to as DES 2.

(2) Animal Test

Figure 2:
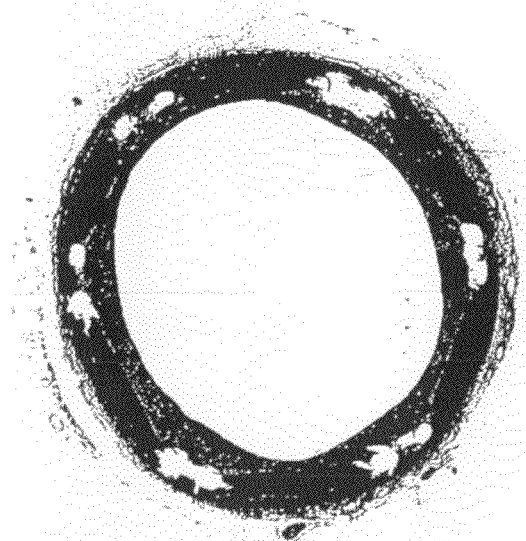
FIG. 2 is a diagram of a pathological sample showing a section of a blood vessel of DES2.

The six stents (DES 2), prepared by the methods described in Preparing Reference Example (1-2) above, were implanted in 6 coronary arteries (LAD, LCX) of 6 heads of Clawn miniature pigs (weighing 25 to 36 kg) in accordance with the procedures employed in the Animal Test 1 described in the specification of International Patent Application PCT/JP2008/002410 and, 28 days thereafter, those pigs were dissected to remove hearts which were fixed in formalin. Thereafter, stented vessels were dissected from the hearts. After fixation of them with acrylic resin, the test pieces were prepared by cutting out of the fixed tissues at three locations, corresponding to both of distal ends and intermediate portion of the respective stents, to provide a test piece of 6 μm in thickness. Those test pieces were subsequently stained according to the hematoxylin eosin staining method and the Elastica-van Gieson method, followed by evaluation to determine the area stenosis (%) and the rate of endothelialization (%). The area stenosis with the DES 2 was found to be 28±8%, and the rate of endothelialization exhibited by the DES 2 was found to be 100%, showing that injuries to the inner wall of blood vessels, which occurred at the time of placement of the stents, were completely repaired. An example of the histopathological samples of the DES 2 is shown in FIG. 2.

As shown above, the animal test, which has been discussed hereinbefore, are believed to have proven that when the stent (DES2) was implanted in the coronary artery, the argatroban so released therefrom could effectively inhibit the vascular intimal hyperplasia and, within one month after stenting, the inner wall of vessels could be completely covered by the endothelial cells.

Example 1

A mixed solution (coating solution) was prepared by dissolving 100 mg of argatroban and 200 mg of L-lactic acid/6-hydroxy hexanoic acid (alias: ε-hydroxy caproic acid) copolymer (mole ratio: 50/50) uniformly with the use of 20 mL of 2,2,2-trifluoroethanol. A stent body (hereinafter referred to as Stent 1) of such a design as shown in FIG. 1 and having the total surface of 0.70 cm$^2$, a length of 17 mm, an inner diameter of 3 mmφ when dilated, and an outer diameter of 1.55 mmφ when processed, was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 592 μg of the mixture containing the argatroban and copolymer referred to above was coated on those stent bodies (Average thickness of the coated layer: 7.0 μm). Those stent bodies are hereinafter referred to as DES-A1.

Example 2

A mixed solution (coating solution) was prepared by dissolving 120 mg of argatroban and 180 mg of L-lactic acid/6-hydroxy hexanoic acid (alias: ϵ-hydroxy caproic acid) copolymer (mole ratio: 50/50) uniformly with the use of 20 mL of 2,2,2-trifluoroethanol. The Stent 1 was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 594 μg of the mixture containing argatroban and the copolymer referred to above was coated on those stent bodies (Average thickness of the coated layer: 7.1 μm). Those stent bodies are hereinafter referred to as DES-A2.

Example 3

A mixed solution (coating solution) was prepared by dissolving 80 mg of argatroban and 220 mg of L-lactic acid/6-hydroxy hexanoic acid (alias: ϵ-hydroxy caproic acid) copolymer (mole ratio: 75/25) uniformly with the use of 20 mL of 2,2,2-trifluoroethanol. The Stent 1 was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 602 μg of the mixture containing argatroban and the copolymer referred to above was coated on those stent bodies (Average thickness of the coated layer: 7.2 μm). Those stent bodies are hereinafter referred to as DES-A3.

Example 4

A mixed solution (coating solution) was prepared by dissolving 60 mg of argatroban and 240 mg of L-lactic acid/6-hydroxy hexanoic acid (alias: ϵ-hydroxy caproic acid) copolymer (mole ratio: 75/25) uniformly with the use of 20 mL of 2,2,2-trifluoroethanol. The Stent 1 was mounted on a mandrel of a spray type coating apparatus. The coating solution so prepared was sprayed from the nozzle at a rate of 20 μL/min. and the stent body, held 99 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 592 μg of the mixture containing argatroban and the copolymer referred to above was coated on those stent bodies (Average thickness of the coated layer: 7.0 μm). Those stent bodies are hereinafter referred to as DES-A4.

Example 5

A mixed solution (coating solution) was prepared by dissolving 100 mg of D-lactic acid/L-lactic acid copolymer (mole ratio: 75/25) uniformly with the use of 20 mL of 2,2,2-trifluoroethanol. The DES-A2 obtained in Example 2 was mounted on a mandrel of a spray type coating apparatus. The coating solution so prepared was sprayed from the nozzle at a rate of 10 μL/min. and the stent body, held 9 mm below the nozzle and rotated at a rate of 120 rpm together with the mandrel, was reciprocatingly moved to allow the sprayed solution to be applied for about 2 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 5 stent bodies were coated in the manner described above. When those stent bodies were measured to the unit of μg by means of a microbalance, it has been found that an average quantity of 40 μg of the mixture containing argatroban and the copolymer referred to above was coated on those stent bodies (Average thickness of the coated layer: 0.48 μm). Those stent bodies are hereinafter referred to as DES-A5.

<Drug Release Test 1>

The drug elution rate of each of five types of the drug coated stents prepared respectively as described in Examples 1 to 5 was measured. For this purpose, each of those drug coated stents was mounted on a balloon catheter of 3 mm in diameter and 20 mm in length and was then sterilized with an ethylene oxide gas (EOG). After the sterilization, the balloon catheter carrying the respective drug coated stent was inflated at about 12 atmospheres for 30 seconds to expand to have a diameter of 3 mm. Three drug coated stents were placed within sealed clean glass containers one by one and 30 mL of a phosphate buffered saline having a pH value of 7.4 was added to each of those glass containers. In a condition in which those stents were completely immersed in the solutions, those containers were shaken within a temperature-controlled oven at 37° C.

The UV absorption (331 nm) of the elute obtained at intervals of a predetermined time was measured using a commercially available ultraviolet visible spectrometer, UV-2450 manufactured by and available from Shimadzu Corporation to determine the absorbance exhibited by argatroban. An analytical curve was prepared using phosphate buffered salines each containing argatroban in a concentration of 0.001% and 0.0001%, respectively, and the absorbance was converted into concentration to determine the released quantity of argatroban per 1 $cm^2$ of the stent surface area. Results are tabulated in Table 1 below.

TABLE 1

Drug Elution Rates Exhibited by DES-A.

| Stents | Drug elution rate after 0 to 24 hours of immersion ($\mu g/cm^2$ per day) | Drug elution rate after 24 to 48 hours of immersion ($\mu g/cm^2$ per day) | Drug elution rate after 48 to 72 hours of immersion ($\mu g/cm^2$ per day) | Drug elution rate after 72 to 96 hours of immersion ($\mu g/cm^2$ per day) |
|---|---|---|---|---|
| DES-A1 | 66 | 27 | 19 | 12 |
| DES-A2 | 79 | 31 | 26 | 20 |
| DES-A3 | 94 | 21 | 10 | 6 |
| DES-A4 | 31 | 7 | 7 | 6 |
| DES-A5 | 53 | 24 | 18 | 14 |

Table 1 above makes it clear that no burst-like abrupt release of the drug within 24 hours subsequent to the immersion into the phosphate buffered saline was found in each of the drug coated stents (DES-A1 and DES-A2) in Example 1 and that the released quantity of argatroban within 24 to 96 hours subsequent to the immersion into the phosphate buffered saline was 12 $\mu g/cm^2$ or higher, having exhibited an advantageous release of the argatroban. Moreover, although burst-like abrupt release of the drug within 24 hours subsequent to the immersion into the phosphate buffered saline was found in the drug coated stent (DES-A3), the released quantities of argatroban within 24 to 48 hours and within 48 to 72 hours subsequent to the immersion into the phosphate buffered saline were appropriate, and the drug coated stent (DES-A4) also showed an advantageous release of the argatroban over a long period. The drug coated stent (DES-A5) in which the second coated layer was formed on the drug coated stent (DES-A2) also showed a good release of the argatroban.

Comparative Example 1

A mixed solution (coating solution) was prepared by dissolving 140 mg of argatroban and 160 mg of poly(D,L-lactic acid-co-glycolic acid) (mole ratio: 50/50) uniformly with the use of 20 mL of 2,2,2-trifluoroethanol. A stent body (hereinafter referred to as Stent 1) of such a design as shown in FIG. 1 and having the total surface of 0.70 $cm^2$, a length of 17 mm, an inner diameter of 3 mmφ when dilated, and an outer diameter of 1.55 mmφ when processed, was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. 30 stent bodies were coated in the manner described above under the same conditions. When those stent bodies were measured to the unit of μg by means of a microbalance, it has been found that an average quantity of 619 μg of the mixture containing argatroban and the copolymer referred to above was coated on those stent bodies. (Average thickness of the coated layer: 7.4 μm) Those stent bodies are hereinafter referred to as REF-1.

Comparative Example 2

A mixed solution (coating solution) was prepared by dissolving 100 mg of argatroban and 200 mg of poly(6-hydroxy hexanoic acid) uniformly with the use of 20 mL of 2,2,2-trifluoroethanol. The Stent 1 was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 586 μg of the mixture containing argatroban and the polymer referred to above was coated on those stent bodies. (Average thickness of the coated layer: 7.0 μm) Those stent bodies are hereinafter referred to as REF-2.

Comparative Example 3

A mixed solution (coating solution) was prepared by dissolving 100 mg of argatroban, 180 mg of poly(6-hydroxy hexanoic acid) and 20 mg of diethyl tartrate (low-molecular compound) uniformly with the use of 20 mL of 2,2,2-trifluoroethanol. The Stent 1 was mounted on a mandrel of a spray type coating apparatus. The coating solution so prepared was sprayed from the nozzle at a rate of 20 μL/min. and the stent body, held 9 mm below the nozzle and rotated at a rate of 120 rpm together with the mandrel, was reciprocatingly moved to allow the sprayed solution to be applied for about 4 minutes to a zone of the stent body ranging from one end thereof to an intermediate portion thereof. After the coating in the manner described above, the stent body was dried for 10 minutes with the stream of a nitrogen gas, followed by coating of the remaining zone of the stent body. The stent body, which had been completely coated over the entire surface thereof, was, after having been dried for about 1 hour, dried at 60° C. for 17 hours within a temperature-controlled vacuum drying oven to remove the solvent completely. Under the same conditions 10 stent bodies were coated in the manner described above. When those stent bodies were measured to the unit of μg by means of a microbalance, it has been found that an average quantity of 591 μg of the mixture containing argatroban, the low-molecular compound, and the polymer referred to above was coated on those stent bodies (Average thickness of the coated layer: 7.0 μm). Those stent bodies are hereinafter referred to as REF-3.

In accordance with the method described in <Drug Release Test 1>, the drug elution rate of each of three types of the drug coated stents prepared respectively as described in Comparative Examples 1 to 3 was measured, and the results was shown in Table 2. Neither of the stents has been able to attain the necessary elution rate of the drug during the drug elution period to inhibit blood vessel inner membrane thickening (3 $\mu g/cm^2$ per day or higher).

TABLE 2

Drug Elution Rates Exhibited by REF.

| Stents | Drug elution rate after 0 to 24 hours of immersion ($\mu g/cm^2$ per day) | Drug elution rate after 24 to 48 hours of immersion ($\mu g/cm^2$ per day) | Drug elution rate after 48 to 72 hours of immersion ($\mu g/cm^2$ per day) | Drug elution rate after 72 to 96 hours of immersion ($\mu g/cm^2$ per day) |
|---|---|---|---|---|
| REF-1 | 374 | 1 | 0 | 0 |
| REF-2 | 4 | 0 | 0 | 0 |
| REF-3 | 9 | 2 | 1 | 0 |

Industrial Applicability

Since the sustained release of the vascular intimal hyperplasia inhibitor which does not inhibit proliferation of endothelial cells for a predetermined period can be accomplished by the stent according to the present invention, the stent can be used effectively to treat heart disease and others. Accordingly, the stent has various industrial applicabilities in the field of drugs and medicines, medical materials, medical apparatuses, and the manufacture thereof.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A drug-eluting stent consisting essentially of:
   a stent body of a cylindrical configuration having outer and inner surfaces, the stent body being formed from a metallic material and a surface thereof being optionally activated with a surface treatment, and
   a coated layer coating at least the outer surface of the stent body, the coated layer being a single coated layer, a back surface of the coated layer contacting a surface of the metallic material and a front surface of the coated layer being configured to be in contact with blood, and the coated layer being prepared of a composition comprising a polymer and a drug,
   the composition not containing a lipid-soluble low-molecular weight compound at a ratio of 1 part by weight or more relative to 100 parts by weight of the polymer
   the drug being a vascular intimal hyperplasia inhibitor which does not inhibit proliferation of endothelial cells, the weight compositional ratio (Y/X) of the vascular intimal hyperplasia inhibitor (Y) based on the polymer (X) being within the range of 1/9 to 6/4,
   the polymer (X) being a copolymer of lactic acid (monomer A) and a terminal hydroxy straight alkyl carboxylic acid having 3 to 8 carbon atoms (monomer B), and
   the copolymerization mole ratio (A/B) of the monomer A and the monomer B being within the range of 8/2 to 2/8.

2. The drug-eluting stent as claimed in claim 1, in which the inhibitor comprises argatroban as an essential component.

3. The drug-eluting stent as claimed in claim 1, in which the single coated layer has a thickness within the range of 1 to 20 μm.

4. The drug-eluting stent as claimed in claim 1, in which the monomer B is 6-hydroxy hexanoic acid.

5. The drug-eluting stent as claimed in claim 1, in which the low-molecular compound has a molecular weight of 400 or less.

6. A method of making a stent comprising a stent body and a coated layer, which comprises:
   applying the composition recited in claim 2 to at least an outer surface of the stent body with the use of a solution containing a solvent comprising a fluorinated alcohol as a major component, and
   removing the solvent to thereby form the coated layer.

7. A method of controlling the elution rate of argatroban from a stent in which the composition recited in claim 2 is applied to a surface of the stent body with the use of the solution comprising the composition dissolved with a solvent, followed by removal of the solvent to thereby form a single coated layer, the solvent dissolving the composition containing a fluorinated alcohol as a major component, and optionally containing a non-fluorinated alcohol, a ketone, an ester, or a halogenated hydrocarbon, and
   in which the elution rate is controlled by changing the copolymerization ratio of the monomer A and the monomer B in the copolymer of lactic acid (monomer A) and a terminal hydroxy straight alkyl carboxylic acid having 3 to 8 carbon atoms (monomer B), and/or by changing the concentration of the fluorinated alcohol in the solvent by adding a non-fluorinated alcohol, a ketone, an ester, or a halogenated hydrocarbon to the solvent.

8. A method of inhibiting vascular intimal hyperplasia, which comprises:
   placing a stent recited in claim 2, within a blood vessel; and
   causing argatroban to be released from the stent to thereby inhibit the vascular intimal hyperplasia without inhibiting proliferation of endothelial cells.

* * * * *

UNITED STATES PATENT AND TRADEMARK OFFICE
CERTIFICATE OF CORRECTION

| | | |
|---|---|---|
| PATENT NO. | : 8,591,571 B2 | Page 1 of 1 |
| APPLICATION NO. | : 13/137560 | |
| DATED | : November 26, 2013 | |
| INVENTOR(S) | : Ikuo Omura et al. | |

It is certified that error appears in the above-identified patent and that said Letters Patent is hereby corrected as shown below:

In the Claims

In Column 18, Line 8, In Claim 1, delete "polymer" and insert -- polymer, --, therefor.

Signed and Sealed this
Twenty-fifth Day of March, 2014

Michelle K. Lee
*Deputy Director of the United States Patent and Trademark Office*